United States Patent
Olivier-Bourbigou et al.

(10) Patent No.: US 7,754,904 B2
(45) Date of Patent: Jul. 13, 2010

(54) PROCESS FOR CO-PRODUCING OLEFINS AND DIESTERS OR DIACIDS BY HOMOMETHATHESIS OF UNSATURATED FATS IN NON-AQUEOUS IONIC LIQUIDS

(75) Inventors: Hélène Olivier-Bourbigou, Saint Genis Laval (FR); Gérard Hillion, Herblay (FR); Christophe Vallee, Fontaine (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 842 days.

(21) Appl. No.: 11/626,082

(22) Filed: Jan. 23, 2007

(65) Prior Publication Data
US 2007/0179302 A1    Aug. 2, 2007

(30) Foreign Application Priority Data
Jan. 24, 2006  (FR)  ................... 06 00645

(51) Int. Cl.
*C11C 1/00*  (2006.01)
(52) U.S. Cl. ................. 554/165; 554/161; 554/164
(58) Field of Classification Search ............... 554/161, 554/164, 165
See application file for complete search history.

(56) References Cited
U.S. PATENT DOCUMENTS

| | | | |
|---|---|---|---|
| 5,675,051 A | 10/1997 | Chauvin et al. | |
| 5,969,170 A | 10/1999 | Grubbs | |
| 6,756,500 B1 | 6/2004 | Gurtler et al. | |
| 2005/0107626 A1 | 5/2005 | Herrmann | |

FOREIGN PATENT DOCUMENTS

| | | |
|---|---|---|
| EP | 1 035 093 A | 9/2000 |
| WO | WO 96/04289 A | 2/1996 |
| WO | WO 99/51344 A | 10/1999 |

OTHER PUBLICATIONS

Olivier-Bourbigou H et al., Ionic Liquids: Perspectives For Organic and Catalytic Reactions, Journal of Molecular Catalysis, 2002, pp. 419-437.

*Primary Examiner*—Deborah D Carr
(74) *Attorney, Agent, or Firm*—Millen, White, Zelano & Branican, P.C.

(57) ABSTRACT

A process is described in which an unsaturated fat is reacted in a homometathesis reaction in the presence of at least one non-aqueous ionic liquid to produce both an olefinic fraction and a composition of monoalcohol diesters or diacids.

Particular application to a mixture of esters of an oleic sunflower seed oil or an oleic rapeseed oil, the process producing both an olefinic fraction and a composition of monoalcohol diesters or diacids wherein, in general, more than half of its chains is constituted by unsaturated $C_{18}$ chains.

23 Claims, No Drawings

PROCESS FOR CO-PRODUCING OLEFINS AND DIESTERS OR DIACIDS BY HOMOMETHATHESIS OF UNSATURATED FATS IN NON-AQUEOUS IONIC LIQUIDS

DOMAINS OF THE INVENTION

The invention relates to the co-production of olefins and diesters or diacids by homometathesis of unsaturated fats in the presence of a catalyst and at least one non-aqueous ionic liquid.

PRIOR ART

The olefin metathesis reaction is a reaction which is well known in organic chemistry. That reaction, which is carried out in the presence of a suitable catalytic system, consists of exchanging alkylidene groups between two olefins in accordance with the following equations:

1) The first case, "cross metathesis" (i.e. metathesis between two different olefins):

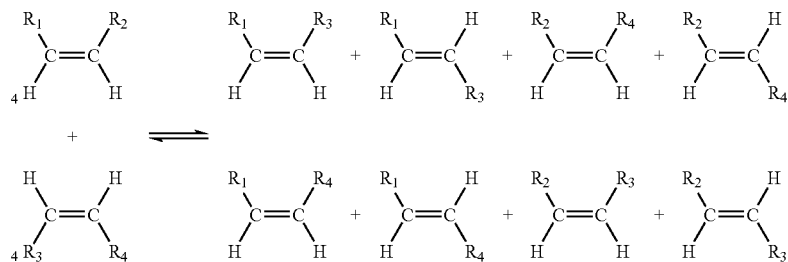

2) The second case, "self metathesis" or "homometathesis" (i.e. metathesis of one molecule of olefin on another molecule of the same olefin):

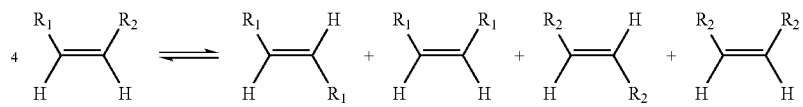

The olefin metathesis reaction is an equilibrated reaction. It may occur in the presence of a wide variety of catalysts, usually based on transition metals from groups IVA to VIII, including tungsten, molybdenum, rhenium and ruthenium, either in the homogeneous phase or in the heterogeneous phase. A number of reviews and scientific works deal with this aspect. Examples which may be cited are:

K J Ivin and J C Mol in "Olefin metathesis and metathesis polymerization", San Diego, Academic Press (1997);

"Handbook of metathesis", R H Grubbs (ed), Wiley-VCH, Weinheim (2003);

J C Mol, "Industrial applications of olefin metathesis", J Mol Catal 213, 39 (2004);

D Séméril and P H Dixneuf, in "Novel metathesis chemistry: Well defined initiator systems for specialty chemical synthesis, tailored polymers and advanced material applications", Y Imamoglu and L Bencze (Eds), Kluwer Academic Publishers, The Netherlands (2003), 1-21.

If the olefin is an unsaturated fatty acid ester represented, for example, by methyl oleate, the reaction leads to the production of one unsaturated olefin and one unsaturated diester. The reaction can be written as follows,

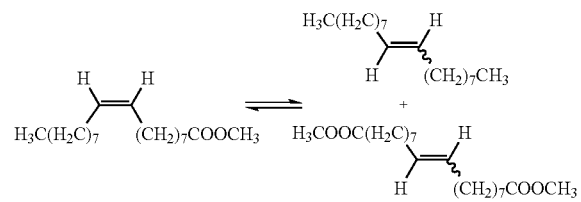

This reaction is of great potential interest as we can envisage starting from a material which is essentially of vegetable or animal origin, and is thus renewable, to produce products such as an unsaturated diester and a long chain olefin. In the particular case envisaged, the unsaturated diester is the methyl diester of octadec-9-ene-1,18-dioic acid which has potential in the manufacture of certain polymers (polyesters, polyamides), and the long chain olefin is octadec-9-ene, which may be dimerized and hydrogenated to produce 10,11-dioctyleicosane which has interesting lubricant properties.

This homometathesis reaction applied to fatty acid esters has been reported in many publications and scientific reviews. The most recent examples which can be cited are:

"Application of olefin metathesis in oleochemistry: an example of green chemistry", J C Mol, Creen Chemistry, 4, 5-13 (2002);

"The metathesis of polyunsaturated fatty esters using the homogeneous $W(O-2,6-C_6H_3X_2)_2Cl_4/Me_4Sn$ catalytic systems", by B B Marvey et al, J Mol Catal 213, 151-157 (2004);

"Technological and economical aspects of the metathesis of unsaturated esters" by M Sibeijn et al, JAOCS, 71, 6 (1994);

"Polymer and surfactants on the basis of renewable resources", by S Warwel et al, Chemosphere 43, 39-48 (2001);

"Catalysis metathesis of unsaturated fatty acid esters and oils", by J C Mol, Topics in Catalysis, 27, 1 (2004).

Various types of catalyst have been described for carrying out this transformation. The first systems were homogeneous, based on tungsten and tetraalkyl tins, for example $WCl_6$/$SnMe_4$. This was followed by heterogeneous systems based on rhenium activated by tetraalkyl tins. However, such systems have the disadvantage of using co-catalysts, generally based on tin, which may contaminate the reaction products. More recently, homogeneous "well defined" systems using no co-catalyst and based on metal-carbenes (M=C) have been described, the metal being tungsten or molybdenum. However, the main difficulty encountered with all of these systems remains their poor compatibility with functional groups such as acids or esters, for example those present in vegetable oils. This generally means low activity and rapid deactivation of such catalytic systems.

Complexes based on ruthenium have rapidly proved themselves to be very interesting because of their tolerance of a wide range of functional groups. That property, coupled with an activity which is often high, explains their major development in the field of polymer synthesis and in organic synthesis.

Their use to catalyze the metathesis of vegetable oils has been studied widely. The following references can be provided:

International patent application WO-A-96/04289 (R Grubbs et al) describes the homometathesis of methyl oleate and oleic acid with complexes of type 1 (FIG. 1 below). The reaction produces an mixture at equilibrium comprising an olefin and an unsaturated diester or diacid;

International patent application WO-A-99/51344 (W Herrmann et al), U.S. Pat. No. 6,635,768 (Herrmann et al) and US patent application US-A1-2004/0095792 (Herrmann et al) describe the use of complexes analogous to type 2 (FIG. 1 below) to catalyze the homometathesis of methyl oleate and the metathesis of methyl oleate with 1-octene. The latter complexes may be more active but also show isomerizing activity of the double bond;

International application WO-A-02/076920 (Newman et al) describes the use of type 3 ruthenium complexes (FIG. 1 below) in a homogeneous medium or a medium supported on polymers, for example of the polystyrene type. The special feature of such complexes compared with those above is that they carry a chelated ligand. Clearly, immobilizing the complex on a solid support considerably reduces the activity of the system.

Type 1 Complexes. L1 and L2 are Phosphines

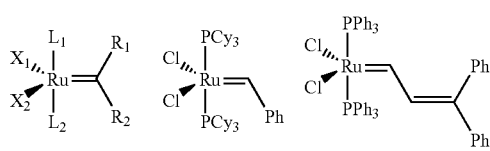

Examples of Type 1 Complexes

Type 2 Complexes. L1 or L2 is a Heterocyclic Carbene

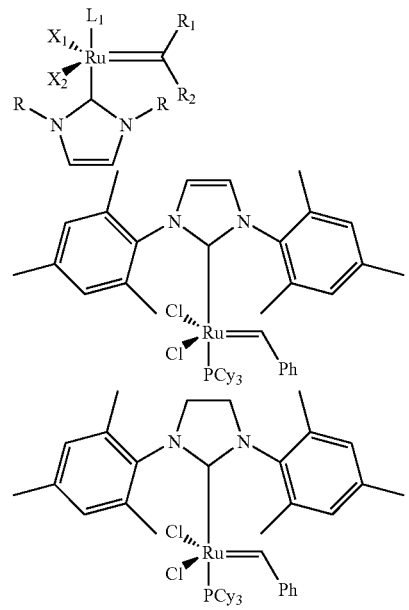

Examples of Type 2 Complexes

Type 3 Complexes

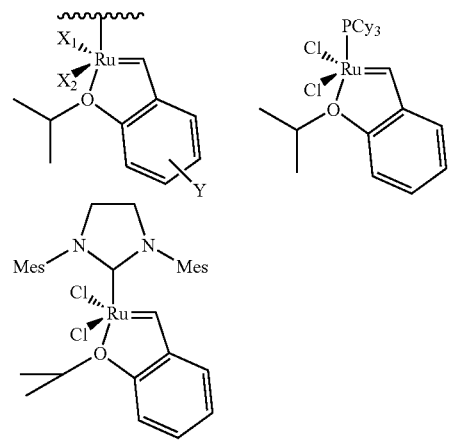

Examples of Type 3 Complexes

FIG. 1

One of the principal difficulties of such systems based on ruthenium is their service life, which is too short. Using them in the homogeneous phase produces the most active complexes, but raises the problem of separating the reaction products and recycling them.

One interesting approach consists of immobilizing the catalyst in a liquid phase (solvent) from which the products can readily be separated either by distilling or by decanting if the products are only slightly miscible with the solvent.

Non-aqueous ionic liquids with general formula $Q^+A^-$ have been shown to be particularly advantageous solvents for this application. They have a very low vapour tension (do not distil) and physico-chemical properties which can be modified as a function of the anion and cation in them (see, for example, H Olivier-Bourbigou, L Magna, *J. Mol Catal A, Chem*, 2002, vol 182, p 419).

Immobilizing ruthenium-based catalysts in ionic liquids has been described, but little literature exists in this area. An example which may be cited is European patent EP-B-1 035 093. However, the described applications only concern cases of ring closing or ring opening metathesis (RCM or ROMP).

Further, one of the principal problems of this homometathesis reaction resides in the conversion yields. Since this reaction is an equilibrated reaction, the maximum yield of products obtained is 50%. A solution which could increase the conversion by displacing the equilibrium would thus be particularly desirable.

Homometathesis of unsaturated fats in ionic liquids has not been described. Since the enthalpy variations associated with this type of reaction are very small, the result at thermodynamic equilibrium is close to a statistical distribution of the alkylidene groups. Thus, for the homometathesis of methyl oleate, the composition of the mixture at equilibrium is close to 50% of the starting products, 25% of the long chain $C_{18}$ olefin and 25% of diester. For industrial application, it is thus necessary to recycle the unconverted reagent after separating the reaction products.

Developing a process for homometathesis of unsaturated fats which is economically viable thus involves:
- developing a stable catalyst which does not isomerize the double bond to a great extent;
- a process in which the long chain olefin co-produced during the reaction is selectively extracted from the reaction medium to displace the equilibrium in the direction of formation of the long chain olefin and the diester or diacid;
- a process in which the catalyst can be recycled and re-used.

Aim of the Invention

The invention pertains to a process involving homometathesis of unsaturated fats in the presence of a catalyst comprising at least one ruthenium compound and in the presence of at least one non-aqueous ionic liquid, for example.

More particularly, the invention concerns a process for the homometathesis of fats selected from monoalcohol esters of oleic sunflower oils and oleic rapeseed oils and mixtures of the corresponding acids.

In this novel process, the catalyst (for example based on a ruthenium complex) is immobilized and stabilized in the non-aqueous ionic liquid in which the olefins produced are only slightly miscible. These are thus extracted during the reaction, and as they are formed, into a second phase.

In this novel process, the reaction products may be separated readily from the ionic liquid containing the catalyst either by distillation, because of the non-volatility of the ionic liquid, or by decanting due to the low solubility of the olefins formed in the ionic liquid. The catalyst remains immobilized and stabilized in the ionic liquid. This latter containing the catalyst may be recycled and re-used.

This process is used to obtain particular compositions of products which are separated into distinct fractions each having a different use.

DETAILED DESCRIPTION OF THE INVENTION

The Feed

The metathesis process of the invention is applicable to any fat comprising at least one carboxylic monoacid or a monoester containing 12 to 22 carbon atoms and comprising at least one ethylenically unsaturated bond.

The skilled person will be aware that fatty acids are usually obtained by hydrolysis of oils or fats in an acid medium.

The fatty acid esters may be obtained either by esterification of fatty acids or by direct transesterification of oils (or triglycerides) with a monohydroxylated saturated aliphatic compound such as methanol, ethanol, propanol or, more generally, any monoalcohol containing 1 to 8 carbon atoms.

Fatty acids are the major components of oils of plant or animal origin. They are rarely obtained in the pure natural state and are always constituted by mixtures of several fatty acids.

The principal monounsaturated fatty acids which are naturally encountered in oils usually carry the unsaturated bond in the cis form and in the Δ9 position (the position of the unsaturated bond counted from the carboxylic group).

Examples from this family are: lauroleic acid (dodecen-9c-oic acid), myristoleic acid (tetradecen-9c-oic acid), palmitoleic acid (hexadecen-9c-oic acid), oleic acid (octadecen-9c-oic acid), gadoleic acid (eicosen-9c-oic acid) and cetoleic acid (docosen-9c-oic acid).

We also find in the natural state positional isomers of the unsaturated bond of oleic acid, such as cis-vaccenic acid (octadecen-11c-oic acid) as well as petroselinic acid (octadecen-6c-oic acid), other fatty acids where the unsaturated bond is in the (n-9) position [the unsaturated bond position being counted from the terminal methyl group of the fatty chain], such as hypogeic acid (hexadecen-7c-oic acid), gondoic acid (eicosen-11c-oic acid), erucic acid (docosen-13c-oic acid), or nervonic acid (tetracosen-15c-oic acid).

The majority of these acids are minor compounds of certain oils or are present in larger amounts in the seeds of plants the culture of which is still confidential or indeed or very limited.

Trans isomers of monounsaturated fatty acids are also found in the natural state. Vaccenic acid (octadecen-11t-oic acid) may be cited.

Partial hydrogenation of polyunsaturated fats is always accompanied by cis-trans isomerizations. Said isomerizations may also affect all of the monoolefins present. Elaidic acid (9t) and brassidic acid (13t) in particular may be cited, which are respectively the trans isomers of oleic acid and erucic acid.

No monounsaturated acid with a terminal double bond exists in nature. However, undecyenlic acid (undecen-10-oic acid), which results from cracking ricinoleic acid, which is an industrial product used in the synthesis of nylon-11 (Rilsan®), may be an interesting intermediate in homometathesis, as it is very pure, and can primarily provide, in the methyl ester form, a $C_{20}$ monounsaturated diester and ethylene.

It is also possible to cite fatty acids with secondary oxygenated functions, principally with alcohol functions, the principal one of which is ricinoleic acid (hydroxyl-12L-octadecen-9c-oic acid), the principal constituent of castor oil.

After homometathesis, in this case, no monoolefins are produced, but rather a $C_{18}$ olefinic diol with a monounsaturated $C_{20}$ diester.

As no fat of natural vegetable or animal origin exists wherein the fatty chains are exclusively constituted by oleic chains, obtaining a pure oleic acid ester thus necessitates using a separation and purification operation which usually employs distillation or crystallization under difficult conditions and is thus expensive.

There currently exists a need for oils termed "oleic" derived from sunflower and rapeseed varieties. The oleic acid content frequently exceeds 80%. In contrast, the linoleic acid (octadecadien-9c-oic acid) content may attain 10% to 12% and deleteriously affect the quality of products resulting from the homometathesis reaction by producing a large number of diacid isomers and mono- and poly-olefinic compounds.

In a further variation to produce starting materials which are enriched in monounsaturated oleic type fatty acids, selective hydrogenation of mixtures of fatty acids containing $C_{18}$ polyunsaturated acids is carried out. In this case, the product obtained is composed of trans isomers and positional isomers of the double bond. For a dienic fatty acid, in the case of linoleic acid (octadecadien-9c, 12c-oic acid), after a controlled hydrogenation step, a mixture of cis and trans and positional isomers is obtained (Δ9, 10, 11 and 12).

Selective hydrogenation of certain fats can thus enrich the oleic fatty chain content of certain mixtures of fatty acids and hence widen the range of starting materials that may be used for homometathesis.

As an example, selective hydrogenation of oleic sunflower oils or non-oleic rapeseed oils with a fatty acid distribution as follows: palmitic acid (5%), stearic acid (2%), oleic acid (59%), linoleic acid (21%), linolenic acid (9%) and higher $C_{20}$ and $C_{22}$ fatty acids (3%), can produce a composition of close to 90% monounsaturated fatty acids, the complement being principally saturated chains. In this case, from said chemically modified starting material, the homometathesis reaction will principally lead to the formation of two products, octadec-9-ene and the diester (methyl ester of octadec-9-ene-1,18-dioic acid).

The most suitable starting material for the process of the invention should thus be particularly rich in oleic acid or its isomers, fatty chains carrying a single unsaturated bond, to obtain what is mainly a mixture which is rich in the diester of octadec-9-ene-1,18-dioic acid and octadec-9-ene:

The nature of the products obtained and their quantity will thus depend on the fatty acid composition (nature and abundance) of the fatty starting material used.

Examples of Products Produced by Homometathesis on Methyl Esters of Oleic Sunflower Oil The methyl ester of oleic sunflower oil has the following composition:

| | |
|---|---|
| methyl palmitate: | C16:0 = 3% by weight; |
| methyl stearate: | C18:0 = 4% by weight; |
| methyl oleate: | C18:0 = 83% by weight; |
| methyl linoleate: | C18:2 = 10% by weight. |

The products formed in the first reaction can be classified into four distinct categories:
monoolefins;
polyolefins;
unsaturated diesters and monoesters; and
saturated esters.

Octadec-9-ene, dodec-6-ene, pentadec-6,9-diene, octadec-6,9-ene and octadec-6,9,12-triene are the first olefin molecules formed. They may in turn react with themselves and with the mono- and di-unsaturated methyl ester which has not reacted to produce other olefinic molecules, such as tetracos-6,9,12,15,18-pentaene, uneicos-6,9,12,15-tetraene, uneicos-9,12,15-triene, etc. The olefinic fraction obtained comprises at least 80% octadec-9-ene.

The process of the present invention may comprise a step for separating olefins by evaporation. In fact, monoolefins and polyolefins can readily be separated from the reaction medium by distillation, examples being dodec-6-ene, octadec-9-ene, pentadec-6,9-diene, octadec-6,9-diene and octadec-6,9,12-triene, since the boiling point of $C_{18}$ olefins is 34° C. lower than that of the methyl esters of unreacted oleic acid or that of the $C_{18}$ diesters produced.

If the olefin is an ester of a bi-unsaturated fatty acid, such as a methyl ester of linoleic acid, the metathesis reaction will produce mono- or poly-olefins, mono- or poly-unsaturated monoesters and mono- or poly-unsaturated diesters.

The same reactions may be applied to all known unsaturated fatty acid chains, for example the chains of linolenic type tri-unsaturated acids. The number of potentially possible products is higher with a higher number of unsaturated bonds in the chain.

If this reaction of metathesis is applied not to a single chain of fatty acid, for example oleic or linoleic acid as above, but to a mixture of said fatty acid chains, as is the case in reality when products are of vegetable or animal origin, a mixture of products derived from homometathesis of each of the fatty chains involved will be obtained.

In all cases, the saturated fatty acid esters present in the mixtures of fatty chains derived from oleic sunflower oil and oleic rapeseed oil are not reactive in the metathesis reaction and are recovered at the end of the operation.

In the process of the present invention, the previously isolated mixture of olefins may undergo selective distillation to separate the dodec-6-ene, octadec-9-ene, pentadec-6,9-diene, octadec-6,9-diene and octadec-6,9,12-triene.

Olefins containing more than 18 carbon atoms cannot be separated by this technique as their boiling point is too close to that of the oleic esters, saturated fatty acids and diesters produced.

In the composition of monoalcohol diesters or diacids obtained by separation, more than half of the chains is constituted by unsaturated $C_{18}$ chains.

After evaporating off the olefinic fraction (mono- and di olefins), the remaining reaction medium may be reacted again to convert the oleic or linoleic esters which are capable of reacting by homometathesis. It will be recalled that saturated fatty acid ester structures are not involved in the metathesis reaction.

The Ionic Liquid

The non-aqueous ionic solvent is selected from the group formed by liquid salts which have general formula $Q^+A^-$ in which $Q^+$ represents a quaternary ammonium, a quaternary phosphonium, a quaternary guanidinium and/or a quaternary sulphonium and $A^-$ represents any anion which can form a liquid salt at low temperatures, i.e. below 90° C., advantageously at most 85° C., and preferably below 50° C.

The anions $A^-$ are preferably selected from halides, nitrate, sulphate, alkylsulphates, phosphate, alkylphosphates, acetate, halogenoacetates, tetrafluoroborate, tetrachloroborate, hexafluorophosphate, trifluoro-tris-(pentafluoroethyl) phosphate, hexafluoroantimonate, fluorosulphonate, alkylsulphonates (for example methylsulphonate), perfluoroalkylsulphonates (for example trifluoromethylsulphonate), bis(perfluoroalkylsulphonyl)amides (for example bis-trifluoromethylsulphonyl amide with formula $N(CF_3SO_2)_2^-$), tris-trifluoromethylsulphonyl methylide with formula $C(CF_3SO_2)_3^-$, bis-trifluoromethylsulphonyl methylide with formula $HC(CF_3SO_2)_3^-$, arenesulphonates, optionally substituted with halogens or halogenalkyl groups, the tetraphenylborate anion and tetraphenylborate anions the aromatic rings of which are substituted, tetra-(trifluoroacetoxy)-borate, bis-(oxalato)-borate, dicyanamide, tricyanomethylide, and the tetrachloroaluminate anion, or chlorozincate anions.

In the formulae below, $R^1$, $R^2$, $R^3$, $R^4$, $R^5$, and $R^6$ represent hydrogen (with the exception of the $NH_4^+$ cation for $NR^1R^2R^3R^4+$), preferably a single substituent representing hydrogen, or hydrocarbyl radicals containing 1 to 30 carbon atoms, for example alkyl groups, saturated or unsaturated, cycloalkyls or aromatics, aryls or aralcyls, which may be substituted, containing 1 to 30 carbon atoms.

$R^1$, $R^2$, $R^3$, $R^4$, $R^5$ and $R^6$ may also represent hydrocarbyl radicals carrying one or more functions selected from the following: —$CO_2R$, —$C(O)R$, —$OR$, —$C(O)NRR'$, —$C(O)N(R)NR'R''$, —$NRR'$, —$SR$, —$S(O)R$, —$S(O)_2R$, —$SO_3R$, —$CN$, —$N(R)P(O)R'R'$, —$PRR'$, —$P(O)RR'$, —$P(OR)(OR')$, —$P(O)(OR)(OR')$ in which R, R' and R'', which may be identical or different, each represent hydrogen or hydrocarbyl radicals containing 1 to 30 carbon atoms.

The quaternary ammonium and/or phosphonium cations $Q^+$ preferably have one of general formulae $NR^1R^2R^3R^{4+}$ and $PR^1R^2R^3R^{4+}$ or one of general formulae $R^1R^2N=CR^3R^{4+}$ and $R^1R^2P=CR^3R^{4+}$ in which $R^1$, $R^2$, $R^3$ and $R^4$, which may be identical or different, are as defined above.

The quaternary ammonium and/or phosphonium cations may also be derived from nitrogen-containing and/or phosphorus-containing heterocycles comprising 1, 2 or 3 nitrogen and/or phosphorus atoms, with general formulae:

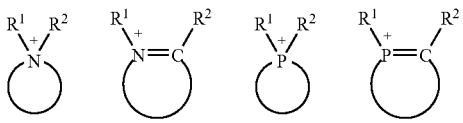

in which the cycles are constituted by 4 to 10 atoms, preferably 5 to 6 atoms, $R^1$ and $R^2$, which may be identical or different, being as defined above.

The quaternary ammonium or phosphonium cation may also have one of the following formulae:

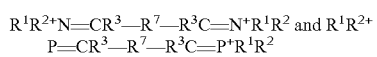

in which $R^1$, $R^2$ and $R^3$, which may be identical or different, are defined as above and $R^7$ represents an alkylene or phenylene radical, Particular groups $R^1$, $R^2$, $R^3$ and $R^4$ which may be mentioned are methyl, ethyl, propyl, isopropyl, primary butyl, secondary butyl, tertiary butyl, amyl, phenyl or benzyl radicals; $R^7$ may be a methylene, ethylene, propylene or phenylene group.

Preferably, the quaternary ammonium and/or phosphonium cation $Q^+$ is selected from the group formed by N-butylpyridinium, N-ethylpyridinium, pyridinium, 3-ethyl-1-methylimidazolium, 3-butyl-1-methylimidazolium, 3-hexyl-1-methylimidazolium, 3-butyl-1,2-dimethylimidazolium, the 1-(2-hydroxyethyl)-3-methylimidazolium cation, the 1-(2-carboxyethyl)-3-methylimidazolium cation, diethylpyrazolium, N-butyl-N-methylpyrrolidinium, N-butyl-N-methylmorpholinium, trimethylphenylammonium, tetrabutylphosphonium and tributyl-tetradecylphosphonium.

The quaternary sulphonium and quaternary guanidinium cations preferably have one of the following general formulae:

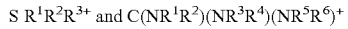

in which $R^1$, $R^2$, $R^3$, $R^4$, $R^5$ and $R^6$, which may be identical or different, are as defined above.

Examples of salts which may be used in the invention that can be cited are 3-butyl-1-methylimidazolium bis(trifluoromethylsulphonyl)amide, 3-butyl-1,2-dimethylimidazolium bis(trifluoromethylsulphonyl)amide, N-butyl-N-methylpyrrolidinium bis(trifluoromethylsulphonyl)amide, 3-butyl-1-methylimidazolium tetrafluoroborate, 3-butyl-1,2-dimethylimidazolium tetrafluoroborate, 3-ethyl-1-methylimidazolium tetrafluoroborate, 3-butyl-1-methylimidazolium hexafluoroantimonate, 3-butyl-1-methylimidazolium trifluoroacetate, 3-ethyl-1-methylimidazolium triflate, 1-(2-hydroxyethyl)-3-methylimidazolium bis(trifluoromethylsulphonyl)amide, 1-(2-carboxyethyl)-3-methylimidazolium bis(trifluoromethylsulphonyl)amide, and N-butyl-N-methylmorpholinium bis(trifluoromethylsulphonyl)amide. These salts may be used alone or as a mixture.

The Catalysts

The catalysts used in the process of the invention to carry out the metathesis of unsaturated fats with excess ethylene may consist of any known metathesis catalyst, in particular catalysts comprising at least one ruthenium compound.

The ruthenium catalysts are preferably selected from charged or uncharged catalysts with general formula:

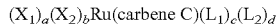

in which:
- a, b, c, d are whole numbers in which a and b equal 0, 1 or 2; c and d equal 0, 1, 2, 3 or 4;
- $X_1$ and $X_2$, which may be identical or different, each represent a mono- or multi-chelating ligand, charged or uncharged; examples which may be cited are halides, sulphate, carbonate, carboxylates, alcoholates, phenates, amides, tosylate, hexafltorophosphate, tetrafluoroborate, bis-triflylamide, tetraphenylborate and derivatives; $X_1$ or $X_2$ may be bonded to $L_1$ or $L_2$ or to "C carbener" to form a bidentate (or chelated) ligand on the ruthenium; and
- $L_1$ and $L_2$, which may be identical or different, are electron-donating ligands such as a phosphine, phosphite, phosphonite, phosphinite, arsine, stilbine, an olefin or an aromatic, a carbonyl compound, an ether, an alcohol, an amine, a pyridine or a derivative thereof, an imine, a thioether or a heterocyclic carbene which, for example, has one of the general formulae of FIG. 2, in which $R_1$, $R_2$, $R_3$, $R_4$ and $R_5$, which may be identical or different, each represent hydrogen or a saturated or unsaturated or aromatic aliphatic hydrocarbon group containing 1 to 12 carbon atoms.

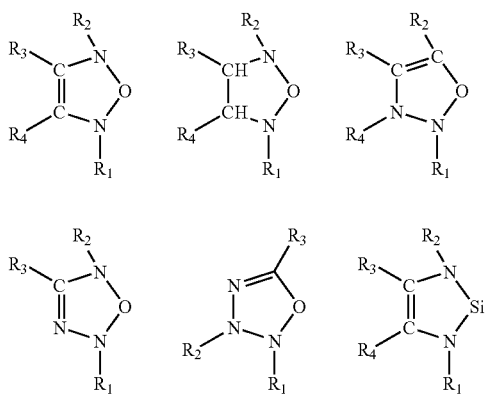

FIG. 2

-continued

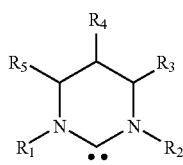

$L_1$ or $L_2$ may be bonded to the "carbene C" to form a bidentate or chelated ligand as indicated in the formula (FIG. 3), in which Z represents a saturated, unsaturated or aromatic, cyclic or non cyclic aliphatic hydrocarbon bi-radical containing 1 to 12 carbon atoms; Y is a heteroelement such as oxygen, nitrogen, sulphur or phosphorus.

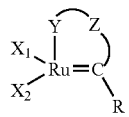

FIG. 3

The "carbene C" may be represented by the general formula: $C(R_1)(R_2)$ in which $R_1$ and $R_2$ are identical or different, such as hydrogen or any other saturated or unsaturated, cyclic, linear or branched or aromatic hydrocarbonyl group. Examples which may be cited are alkylidene ruthenium complexes or cumulene complexes such as vinylidenes, Ru=C=CHR, allenylidenes, Ru=C=C=CR$_1$R$_2$, or indenylidenes.

A functional group which can improve retention of the ruthenium complex in the ionic liquid may be grafted onto at least one of the ligands $X_1$, $X_2$, $L_1$, $L_2$ or onto the carbene C. This functional group may or may not be charged, and is preferably an ester, an ether, a thiol, an acid, an alcohol, an amine, a nitrogen-containing heterocycle, a sulphonate, a carboxylate, a quaternary ammonium, a guanidinium, a quaternary phosphonium, a pyridinium, an imidazolium, a morpholinium or a sulphonium.

Examples of functionalized complexes: suitable positions for the functional group

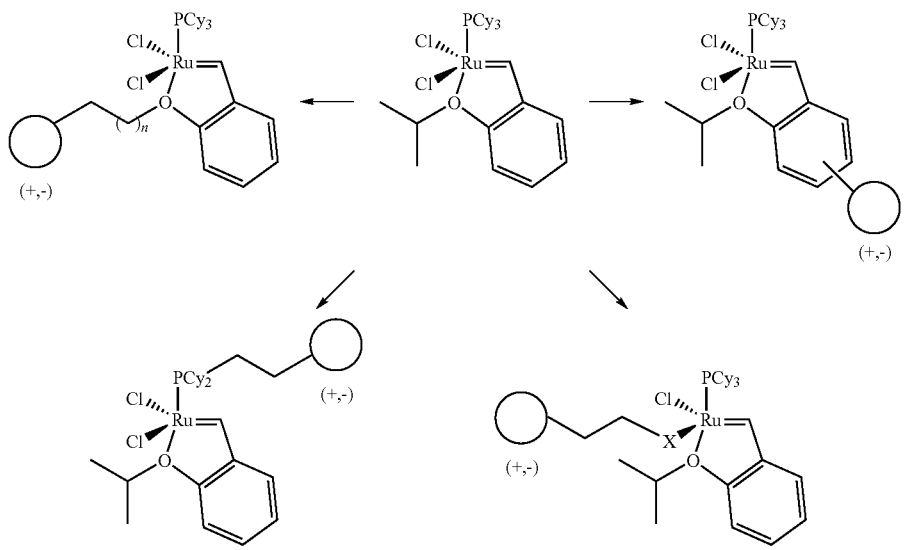

Of these ruthenium derivatives, the following examples may be cited:

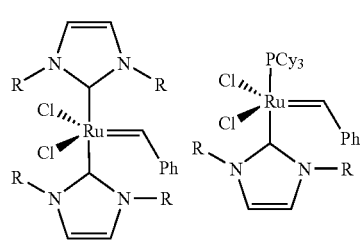

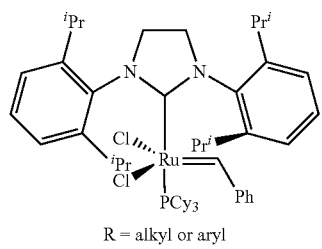
R = alkyl or aryl
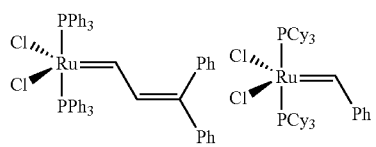
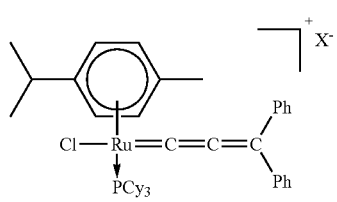
X = OTf, NTf₂, BF₄, PF₆, BPh₄;
Tf = CF₃SO₂
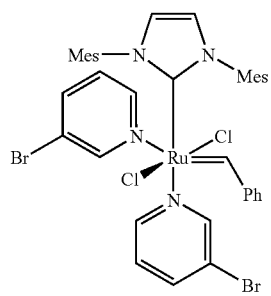
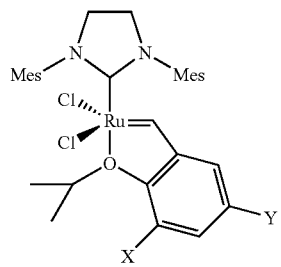
Mes: mesityl; R = C(CF₃)₃, C(CF₃)₂CH₃
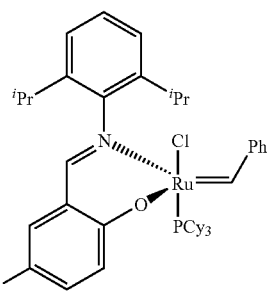
Y = H; X = Ph, OMe, maphtyl
X = H; Y = NO₂, H
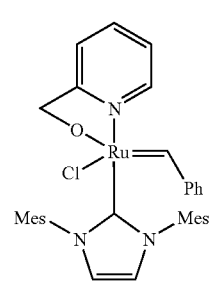
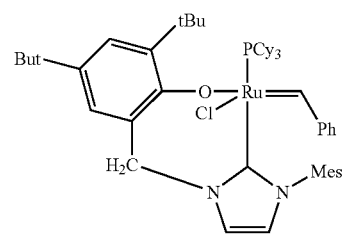
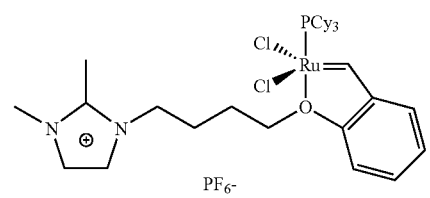
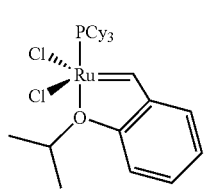
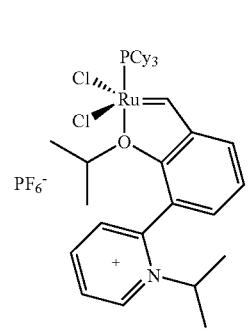
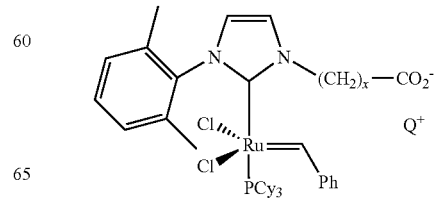

-continued

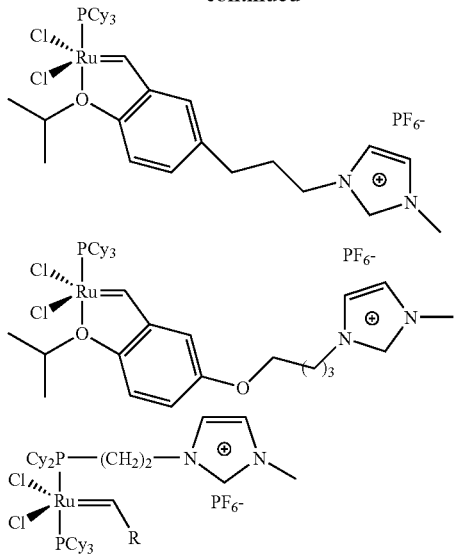

In these formulae, Cy represents the cyclohexyl radical and iPr represents the isopropyl radical. Q+ represents an organic cation (for example ammonium, pyridinium, imidazolium or phosphonium), or an inorganic cation (for example Na+, Li+ or K+).

Implementation

In the process of the invention, metathesis of the starting fat (for example a monoalcohol ester of oleic sunflower oil or oleic rapeseed oil) may be carried out in the absence or presence of an organic co-solvent. In the case in which a solvent or a mixture of solvents is used, its role may be to improve the solubility of the reagents and catalyst in the ionic liquid. It may also act to optimize extraction of the products in a second phase.

Examples of suitable solvents which may be cited are chloroalkanes, such as dichloromethane, chloroform or dichloro- or trichloro-ethane, aromatic solvents such as toluene, xylenes or chlorobenzene, or aliphatic solvents such as heptane or cyclohexane.

The homometathesis reactions of the process of the invention may be carried out in a closed (batch) system, a semi-open system or a continuous system with one or more reaction steps. It is also possible to envisage carrying out the reaction using reactive distillation.

Vigorous agitation ensures good contact between the reagents and the catalytic mixture. The reaction temperature may be in the range 0° C. to +150° C., preferably in the range 20° C. to 120° C.

The operation may be carried out above or below the melting temperature of the medium, the dispersed solid state not being a limitation on the reaction.

The pressure may, for example, be in the range from atmospheric pressure to 50 MPa.

The reaction products may be separated by decanting.

It is also possible to separate the products by distillation if the ionic liquid is sufficiently non-volatile and thermally stable.

The following examples illustrate the invention without limiting scope.

EXAMPLE 1

Biphasic Homometathesis of Methyl Oleate in Ionic Liquid

To a glass reaction flask were added (30 mg, 0.036 mmol, 0.004 eq.) benzylidene-bis(tricyclohexylphosphine)dichlororuthenium, (3mL, 8.84 mmol, 1 eq.) methyl oleate, 1 mL 1-butyl-1-methylpyrrolidinium bis(trifluoromethanesulfonyl)amide with formula [BMPyrr] [NTf$_2$], 2 mL heptane and 0.1 mL of dodecane as internal standard. The mixture was biphasic. It was stirred and heated at 55° C. After 2 hours reaction time, a small aliquot of the liquid upper phase was removed for FID GC analysis. GC analysis indicated that the metathesis reaction had proceeded cleanly, yielding 9-octadecene and dimethyloctadecene-1,18-dioate products. Conversion of methyl oleate to these products was 46 wt %.

EXAMPLE 2

Recycling Experiments.

To a glass reaction flask were added (50 mg, 0.059 mmol, 0.01 eq,) (1,3-Bis-(2,4,6-trimethylphenyl)-2-imidazolidinylidene) dichloro(benzylidene)(tricyclohexylphosphine) ruthenium, (1.5 mL, 4.42 mmol, 1 eq.) methyl oleate, 1 mL 1-butyl-1-methylpyrrolidinium bis(trifluoromethanesulfonyl)amide, 2 mL heptane and 0.1 mL of dodecane as internal standard. The mixture was biphasic. It was stirred at room temperature After 2 hours reaction time, the mixture was decanted. The upper layer was removed and the resulting ionic liquid solution was washed with 2 mL of heptane. A small aliquot of the combined organic liquid was analyzed by GC (entry 1). Fresh methyl oleate (1.5 mL, 4.42 mmol, 1 eq.), 2 mL of heptane and 0.1 mL of dodecane were added to the ionic liquid after each recycle and reaction was allowed to restart at room temperature. GC analysis indicated that the metathesis reaction had proceeded yielding mainly 9-octadecene and dimethyloctadecene-1,18-dioate products. Recycle of the ionic phase was performed 3 times successively without addition of Ru catalyst neither ionic liquid. Conversion of methyl oleate to 9-octadecene and dimethyloctadecene-1,18-dioate products was described in the Table 1.

TABLE 1

Conversion of methyl oleate into 9-octadecene and dimethyloactadecene-1,18-dioate

| Entry | Recycle | Conversion (wt %) |
|---|---|---|
| 1 |  | 55 |
| 2 | first | 54 |
| 3* | second | 50 |
| 4* | third | 50 |

*15 hours reaction time.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 06/00.645, filed Jan. 24, 2006, is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for producing both an olefinic fraction and a composition of diesters or diacids, characterized in that it comprises carrying out a homometathesis reaction on at least one fat comprising at one monobasic carboxylic acid containing 12 to 22 carbon atoms and comprising at least one ethylenically unsaturated bond or a monoester of said monoacid in the presence of a catalyst and in the presence of at least one non-aqueous ionic liquid.

2. A process according to claim 1, characterized in that the non-aqueous ionic liquid is selected from the group formed by liquid salts with general formula $Q^+A^-$ in which $Q^+$ represents a quaternary phosphonium, a quaternary ammonium, a quaternary guanidinium or a quaternary sulphonium and $A^-$ represents any anion which is capable of forming a liquid salt below 90° C.

3. A process according to claim 2, characterized in that the cations $Q^+$ quaternary ammonium or phosphonium, have one of the following formulae:

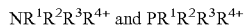

or one of general formulae

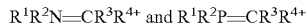

in which $R^1$, $R^2$, $R^3$ and $R^4$, which may be identical or different, represent hydrogen (with the exception of the cation $NH_4^+$ for $NR^1R^2R^3R^{4+}$), hydrocarbyl radicals containing 1 to 30 carbon atoms or hydrocarbyl radicals carrying one or more functions selected from —$CO_2R$, —$C(O)R$, —OR, —$C(O)NRR'$, —$C(O)N(R)NR'R''$, —NRR', —SR, —S(O)R, —$S(O)_2R$, —$SO_3R$, —CN, —N(R)P(O)R'R', —PRR', —P(O)RR', —P(OR)(OR'), —P(O)(OR)(OR') in which R, R' and R'', which may be identical or different, each represent hydrogen or hydrocarbyl radicals containing 1 to 30 carbon atoms.

4. A process according to claim 2, characterized in that the quaternary ammonium and/or phosphonium cations may also be derived from nitrogen-containing and/or phosphorus-containing heterocycles comprising 1, 2 or 3 nitrogen and/or phosphorus atoms, with general formulae:

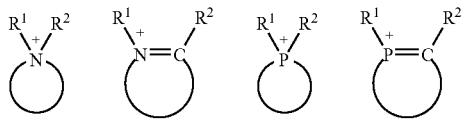

in which the cycles are constituted by 4 to 10 atoms and $R^1$ and $R^2$, which may be identical or different, are as defined above.

5. A process according to claim 2, characterized in that the quaternary ammonium or phosphonium cation has one of the following formulae:

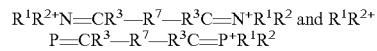

in which $R^1$, $R^2$ and $R^3$, which may be identical or different, are as defined above and $R^7$ represents an alkylene or phenylene radical.

6. A process according to claim 2, characterized in that the quaternary ammonium and/or phosphonium cation $Q^+$ is selected from the group formed by N-butylpyridinium, N-ethylpyridinium, pyridinium, 3-ethyl-1-methylimidazolium, 3-butyl-1-methylimidazolium, 3-hexyl-1-methylimidazolium, 3-butyl-1,2-dimethylimidazolium, the 1-(2-hydroxyethyl)-3-methylimidazolium cation, the 1-(2-carboxyethyl)-3-methylimidazolium cation, diethylpyrazolium, N-butyl-N-methylpyrrolidinium, N-butyl-N-methylmorpholinium, trimethylphenylammonium, tetrabutylphosphonium and tributyl-tetradecylphosphonium.

7. A process according to claim 2, characterized in that the quaternary sulphonium and quaternary guanidinium cations have one of the following general formulae:

in which $R^1$, $R^2$, $R^3$, $R^4$, $R^5$ and $R^6$, which may be identical or different, are defined as in $R^1$, $R^2$, $R^3$ and $R^4$ above.

8. A process according to claim 2, characterized in that the anions $A^-$ are selected from the following anions: halides, nitrate, sulphate, alkylsulphates, phosphate, alkylphosphates, acetate, halogenoacetates, tetrafluoroborate, tetrachloroborate, hexafluorophosphate, trifluoro-tris-(pentafluoroethyl) phosphate, hexafluoroantimonate, fluorosulphonate, alkylsulphonates, perfluoroalkylsulphonates, bis (perfluoroalkylsulphonyl)anides, tris-trifluoromethylsulphonyl methylide with formula $C(CF_3SO_2)_3^-$, bis-trifluoromethylsulphonyl methylide with formula $HC(CF_3SO_2)_3^-$, arenesulphonates, arenesulphonates substituted with halogens or halogenalkyl groups, the tetraphenylborate anion and tetraphenylborate anions the aromatic rings of which are substituted, tetra-(trifluoroacetoxy)-borate, bis-(oxalato)-borate, dicyanamide, tricyanomethylide, as well as the tetrachloroaluminate anion, or chlorozincate anions.

9. A process according to claim 2, characterized in that the ionic liquid is selected from 3-buty-1-methylimidazolium bis (trifluoromethylsulphonylamide, 3-butyl-1,2-dimethylimidazolium bis(trifluoromethylsulphonyl)amide, N-butyl-N-methylpyrrolidinium bis(trifluoromethylsulphonyl)amide, 3-butyl-1-methylimidazolium tetrafluoroborate, 3-butyl-1,2-dimethylimidazolium tetrafluoroborate, 3-ethyl-1-methylimidazolium tetrafluoroborate, 3-butyl-1-methylimidazolium hexafluoroantimonate, 3-butyl-1-methylimidazolium trifluoroacetate, 3-ethyl-1-methylimidazolium triflate, 1-(2-hydroxyethyl)-3-methylimidazolium bis(trifluorometlhylsulphonyl)amide, 1-(2-carboxyethyl)-3-methylimidazolium bis(trifluorometlhylsulphonyl)amide and N-butyl-N-methylmorpholinium bis(trifluoromethylsulphonyl)amide.

10. A process according to claim 1, characterized in that said unsaturated fat which undergoes the homometathesis reaction comprises at least one ester formed between a monocarboxylic acid containing 12 to 22 carbon atoms and comprising at least one ethylenically unsaturated bond and at least one aliphatic monoalcohol containing 1 to 8 carbon atoms.

11. A process according to claim 1, characterized in that said carboxylic monoacid is selected from lauroleic acid, myristoleic acid, palmitoleic acid, oleic acid, gadoleic acid, cetoleic acid, cis-vaccenic acid, petroselinic acid, hypogeic acid, gondoic acid, erucic acid, nervonic acid, vaccenic acid, elaidic acid, brassidic acid, undecylenic acid and ricinoleic acid.

12. A process according to claim 10, characterized in that an unsaturated fat selected from oleic mixtures of monoalcohol esters of oleic sunflower oil and oleic rapeseed oil undergoes the metathesis reaction to produce both an olefinic fraction and a monoalcohol diester composition at least a portion of the chains of which is constituted by unsaturated $C_{18}$ chains.

13. A process according to claim 12, characterized in that the unsaturated fat is enriched in oleic type monounsaturated fatty acids by selective hydrogenation of fatty acids containing $C_{18}$ polyunsaturated acids.

14. A process according to claim 12, characterized in that the composition of oleic sunflower oil fatty acids has the following composition:

| | |
|---|---|
| methyl oleate (C18:1): | about 83% by weight; |
| methyl linoleate (C18:2): | about 10% by weight; |
| methyl palmitate (C16:0): | about 3% by weight; |
| methyl stearate (C18:0): | about 4% by weight. |

15. A process according to claim 1, characterized in that at least one ruthenium compound is used as the catalyst.

16. A process according to claim 15, characterized in that the catalyst is selected from charged or uncharged catalysts with general formula:

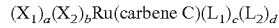

$(X_1)_a(X_2)_b Ru(\text{carbene } C)(L_1)_c(L_2)_d$ in which:
- a, b, c, d are whole numbers in which a and b equal 0, 1 or 2; c and d equal 0, 1, 2, 3 or 4;
- $X_1$ and $X_2$, which may be identical or different, each represent a mono- or multi-chelating ligand, charged or uncharged; $X_1$ or $X_2$ may be bonded to $L_1$ or $L_2$ or to carbene C to form a bidentate ligand on the ruthenium; and
- $L_1$ and $L_2$, which may be identical or different, are donor electron ligands.

17. A process according to claim 1, characterized in that it further comprises a step in which the following are separated:
   an olefinic fraction;
   and a composition of monoalcohol diesters or diacids.

18. A process according to claim 1, characterized in that more than half of the chains in the olefinic fraction obtained by separation is constituted by unsaturated $C_{18}$ chains.

19. A process according to claim 17, characterized in that said olefinic fraction comprises at least 80% octadec-9-ene.

20. A process according to claim 19, characterized in that said olefinic fraction further comprises dodec-6-ene, pentadec-6,9-diene, octadec-6,9-diene and octadec-6,9,12-triene.

21. A process according to claim 17, characterized in that it further comprises a step in which the monoolefins and polyolefins are separated from said olefinic fraction by distillation.

22. A process according to claim 1, characterized in that in the composition of monoalcohol diesters or diacids obtained by separation, more than half of the chains is constituted by unsaturated $C_{18}$ chains.

23. A process according to claim 22, characterized in that in said composition, said monoalcohol contains 1 to 8 carbon atoms.

* * * * *